(12) United States Patent
Chandra et al.

(10) Patent No.: US 9,296,846 B2
(45) Date of Patent: Mar. 29, 2016

(54) POROUS POLYMER COATING FOR TOOTH WHITENING

(75) Inventors: Dinesh Chandra, Philadelphia, PA (US); Andre A. Soshinsky, Randolph, NJ (US); Robert J. Gambogi, Hillsborough, NJ (US); Shu Yang, Blue Bell, PA (US)

(73) Assignees: THE TRUSTEES OF THE UNIVERSITY OF PENNSYLVANIA, Philadelphia, PA (US); JOHNSON & JOHNSON CONSUMER INC., Skillman, NJ (US)

( * ) Notice: Subject to any disclaimer, the term of this patent is extended or adjusted under 35 U.S.C. 154(b) by 1398 days.

(21) Appl. No.: 12/338,357

(22) Filed: Dec. 18, 2008

(65) Prior Publication Data

US 2010/0158960 A1   Jun. 24, 2010

(51) Int. Cl.
| | | |
|---|---|---|
| *A61Q 11/00* | (2006.01) | |
| *A61K 8/02* | (2006.01) | |
| *A61K 6/00* | (2006.01) | |
| *C08F 220/18* | (2006.01) | |
| *A61K 8/81* | (2006.01) | |

(52) U.S. Cl.
CPC ............. *C08F 220/18* (2013.01); *A61K 8/0216* (2013.01); *A61K 8/0279* (2013.01); *A61K 8/8152* (2013.01); *A61Q 11/00* (2013.01); *A61K 6/0002* (2013.01); *A61K 6/0005* (2013.01); *A61K 2800/412* (2013.01)

(58) Field of Classification Search
USPC ........................................... 424/400, 443.486
See application file for complete search history.

(56) References Cited

U.S. PATENT DOCUMENTS

| | | | |
|---|---|---|---|
| 4,433,959 A * | 2/1984 | Faunce ........................ 433/222.1 |
| 4,748,198 A | 5/1988 | Takahashi et al. |
| 4,867,988 A * | 9/1989 | Chernack ....................... 424/490 |
| 5,639,795 A | 6/1997 | Friedman et al. |
| 6,491,898 B1 | 12/2002 | Yamagishi et al. |
| 6,787,629 B2 | 9/2004 | Jia et al. |
| 6,951,463 B2 | 10/2005 | Masuhara et al. |
| 7,090,721 B2 | 8/2006 | Craig et al. |
| 7,156,911 B2 | 1/2007 | Kangas et al. |
| 7,335,250 B2 | 2/2008 | Burtscher et al. |
| 7,361,216 B2 | 4/2008 | Kangas et al. |
| 7,416,735 B2 | 8/2008 | El-Nokaly et al. |
| 2003/0125444 A1 | 7/2003 | Jia et al. |
| 2003/0180344 A1 | 9/2003 | Wise et al. |
| 2004/0086446 A1 | 5/2004 | Jia et al. |
| 2005/0143274 A1 | 6/2005 | Ghosh et al. |
| 2005/0249654 A1 | 11/2005 | Chow |
| 2005/0252413 A1 | 11/2005 | Kangas et al. |
| 2005/0252414 A1 | 11/2005 | Craig et al. |
| 2005/0256223 A1 | 11/2005 | Kolb et al. |
| 2005/0260269 A1 | 11/2005 | Engelbrecht et al. |
| 2005/0272008 A1 * | 12/2005 | Stites ........................... 433/180 |
| 2006/0009540 A1 | 1/2006 | Jia et al. |
| 2006/0024246 A1 | 2/2006 | Maitra et al. |
| 2006/0111465 A1 | 5/2006 | Jia et al. |
| 2006/0147394 A1 * | 7/2006 | Shastry et al. ................... 424/49 |
| 2006/0154195 A1 | 7/2006 | Mather et al. |
| 2006/0204452 A1 | 9/2006 | Velmakanni et al. |
| 2006/0205838 A1 | 9/2006 | Velamakanni et al. |
| 2007/0039519 A1 | 2/2007 | Kangas et al. |
| 2007/0066748 A1 | 3/2007 | Lewandowski et al. |
| 2008/0194722 A1 | 8/2008 | Abuelyaman et al. |
| 2008/0280260 A1 | 11/2008 | Belikov et al. |

FOREIGN PATENT DOCUMENTS

| | | |
|---|---|---|
| JP | 5-58844 | 3/1993 |
| JP | 5-194169 | 8/1993 |
| JP | 9-151123 | 6/1997 |
| JP | 09-175923 A | 7/1997 |
| JP | 2002-541925 A | 12/2002 |
| JP | 2004-196735 A | 7/2004 |
| JP | 2004-522823 A | 7/2004 |
| JP | 2004-330411 A | 11/2004 |
| JP | 2005-247860 A | 9/2005 |
| JP | 2007-501340 A | 1/2007 |
| JP | 2008-508274 A | 3/2008 |
| WO | WO 2005/110339 A1 | 11/2005 |
| WO | WO 2006/116752 A2 | 11/2006 |
| WO | WO 2007/017152 A2 | 2/2007 |
| WO | WO 2007/024652 A2 | 3/2007 |

(Continued)

OTHER PUBLICATIONS

Shakhashiri, Gases of the Air, www.scifun.org, Nov. 2007, printed from http://scifun.chem.wisc.edu/chemweek/pdf/airgas.pdf on Nov. 19, 2011, 2 pages.*

(Continued)

*Primary Examiner* — Gigi Huang
(74) *Attorney, Agent, or Firm* — Scully, Scott, Murphy & Presser, P.C.

(57) ABSTRACT

The present invention relates to a tooth-whitening composition comprising (i) a substantially water-insoluble and substantially non-degradable polymer matrix component capable of adhering to the surface of a tooth, provided that if the polymer matrix component is in non-solid form, it is solidifiable by chemical alteration; and (ii) gas- or liquid-filled pores embedded in said polymer matrix component, wherein at least a portion of said gas- or liquid-filled pores have at least one size dimension in the range of about 70 nm to about 5 microns, and wherein the gas- or liquid-filled pores and polymer matrix component possess a difference in refractive index of at least 0.1. The invention is also directed to a tooth-whitening system containing the above composition in combination with an applicator device. The invention is also directed to methods for applying the tooth-whitening composition onto teeth.

10 Claims, 6 Drawing Sheets

(56) References Cited

FOREIGN PATENT DOCUMENTS

| WO | WO 2008/079758 A1 | 7/2008 |
| WO | WO 2008/083067 A2 | 7/2008 |
| WO | WO 2008/097374 A2 | 8/2008 |

OTHER PUBLICATIONS

Agency for Toxic Substances and Disease Registry (ATSDR), Hydrogen Peroxide, Apr. 2002, printed from http://www.atsdr.cdc.gov/tfacts174.pdf, 2 pages.*

Berge et al., Porosity of resin veneer materials, Acta Odontol Scand. Oct. 1987;45(5), printed from http://www.ncbi.nlm.nih.gov/pubmed/3314314, Abstract only, 1 page.*

Van Soest J.J.G., "The Development of Biopolymer-Based Nanostructured Materials: Plastics, Gels, IPNs, and Nanofoams" Chapter 21:288-303 (2006), edited by Bozell, J.J. et al., "Feedstocks for the Future Renewables for the Production of Chemicals and Materials" *American Chemical Society* (2006).

Wisniewski M. et al., "The Influence of KrF Excimer Laser Irradiation on the Surface of Collagen and Collagen/PVP Films", *International Journal of Photoenergy*, 2006 Article ID 35126:1-7 (2006).

Bunker B.C. et al., "Ceramic Thin-Film Formation of Functionalized Interfaces Through Biomimetic Processing", *Science* 264:48-55 (1994).

Moradian-Oldak J. et al., "Adsorption of Amelogenin Nanopheres onto Charged Surfaces, A Model for Tooth Enamel Matrix Re-construction", *Materials Research Society Symp. Proc. 823*:63-68 (2004).

Scott A., "BASF Develops a Synthetic Tooth Enamel", *Chemical Week*, p. 32 (2002).

De La Isla A. et al., "Nanohybrid Scratch Resistant Coatings for Teeth and Bone Viscoelasticity Manifested in Tribology", *Mat Res Innovat 7*:110-114 (2003).

Lazare S. et al., "Surface Foaming of Collagen, Chitosan and Other Biopolymer Films by KrF Excimer Laser Ablation in the Photomechanical Regime", *Applied Physics A 81*:465-470 (2005).

De La Isla A. et al., "Preparation and Behaviour of a Stain-Protecting Hybrid Coating for Teeth", *International Journal of Polymeric Materials 53*:645-651 (2004).

Zhang Y.H. et al., "Synthesis and Characterization of Polymer Nanofoams", *Key Engineering Materials 334-335*:821-824 (2007).

International search report dated Mar. 9, 2010 for corresponding international application PCT/US09/68486.

Supplementary Extended European Search Report dated Nov. 30, 2012 from related European Application No. 09837918.3.

Wu L. et al., "High-Speed Large Scale Chromatographic Purification of Plasmid DNA with a Novel Giant-Pore Stationary Phase", *Chromatographia 66*(3/4):151-157 (Aug. 2007).

Lu G.D. et al., "Preparation of Porous Polyacrylamide Hydrogels by Frontal Polymerization", *Polymer International 56*:1016-1020 (Apr. 13, 2007).

Caykara T. et al., "Preparation of Macroporous Poly(Acrylamide) Hydrogels by Radiation Induced Polymerization Technique", *Nuclear Instruments and Methods in Physics Research B 265*(1):366-369 (Nov. 17, 2007).

English-language translation of Japanese Notification of Reasons for Refusal dated Apr. 1, 2014 received from related Application No. 2011-542437.

\* cited by examiner

POROUS POLYMER COATING FOR TOOTH WHITENING

FIELD OF THE INVENTION

The present invention relates generally, to the field of dental cosmetics, and more particularly, to teeth-whitening compositions.

BACKGROUND OF THE INVENTION

Whitening of teeth is commonly practiced by chemical treatment of teeth to remove stains (i.e., chromogens) from the teeth. Most chemical treatments make use of bleaching agents, such as hydrogen peroxide, carbamide peroxide, sodium perborate, sodium chlorite, and the like. The chemical treatment is often accompanied by use of abrasive agents, which help desorb or prevent stain adsorption.

However, such stain-removing chemicals possess several drawbacks, such as increased potential for transient teeth whitening-induced sensitivity, increased potential for transient gingival irritation, and the need for repeated or prolonged administration onto teeth to achieve a desired level of teeth whitening. Furthermore, chemical treatment is often ineffective for certain types of dental stains.

Porcelain (ceramic) dental veneers have been used in the art to cover stained teeth to hide dental stains. They provide a non-porous, glazed surface which increases the brilliance of teeth. Though ceramic veneers provide an alternative to the chemical stain removal processes described above, they have the significant drawback of typically having to be custom-designed and custom-fitted for each tooth receiving a veneer. This makes porcelain veneers particularly costly. In addition, the application process typically required a reductive shaping of the teeth to accommodate the porcelain veneers. The reductive shaping of the teeth permanently alters the teeth. Moreover, porcelain veneers are known to be thin and brittle, and are, therefore, well known for being easily damaged during use. For these reasons, porcelain veneers are typically recommended for more severe cases of discolored or unsightly teeth, while chemical teeth-whitening is recommended for the more ordinary and usual discoloration of teeth.

There remains a need in the art for a tooth-whitening process which does not require chemical removal of stains and which mitigates or eliminates the drawbacks of porcelain veneers. There is a particular need in the art for such a tooth-whitening composition that can be applied onto teeth in a cost-effective and facile manner. There would be a particular advantage in a tooth-whitening composition that can be readily applied to teeth without requiring custom-fitting or a reductive processing step, and which is not brittle. Such a composition and method of use can make non-chemical whitening alternatives more mainstream and available to the general public.

SUMMARY OF THE INVENTION

The invention is directed to a tooth-whitening composition that can be readily applied as a coating onto teeth in order to increase the perceived whiteness of the teeth. The composition contains a substantially water-insoluble and substantially non-degradable polymeric matrix (i.e., a continuous phase) containing therein gas-filled or fluid-filled compartments (also referred to herein as pores, voids, or bubbles) within a size range of about 100 nanometers (100 nm) to about 5 microns (5 μm), wherein the gas or liquid and polymer matrix components possess a difference in refractive index of at least 0.1. The difference in refractive index of the gas or liquid pores and polymeric matrix of the composition promotes the diffraction (i.e., scattering) of light, which gives rise to a whiter appearance.

The components of the tooth-whitening composition are such that the tooth-whitening composition is substantially non-degradable in an oral environment, non-toxic, resistant to microbial growth, and capable of adhering to the surface of a tooth. If the polymer matrix (i.e., composition) is in non-solid form, it is solidifiable by chemical alteration. In one embodiment, the composition is applied onto a tooth as a hardenable non-solid composition and is then hardened to a solid film by a solidifying film-forming process. In another embodiment, the composition is applied as a pre-formed (i.e., pre-hardened) solid film onto teeth.

The invention is also directed to a precursor composition for producing the tooth-whitening composition described above, wherein the precursor composition contains a polymer matrix described above and water-soluble and/or biodegradable particles embedded therein such that gas- or liquid-filled pores as described above are produced when the precursor composition is exposed to an aqueous and/or biodegradable environment, such as found in the mouth.

The invention is also directed to tooth-whitening systems which include the tooth-whitening or precursor composition described above and one or more application devices capable of delivering the composition onto a tooth.

The invention is also directed to methods for whitening teeth by applying the tooth-whitening or precursor composition described above onto a tooth such that an adhered solid film of the tooth-whitening or precursor composition is formed on the tooth.

The invention advantageously provides a tooth-whitening composition and resulting process which obviates the need for chemical stain-removal processes. In addition, the tooth-whitening composition is cost-effective and can be applied onto teeth in a facile manner without the need for custom-fitting or a reductive processing step. The resulting coating on teeth provides a brilliant white appearance while being hard, non-brittle, and resistant to degradation and microbial growth.

DETAILED DESCRIPTION OF THE INVENTION

Figure 1:
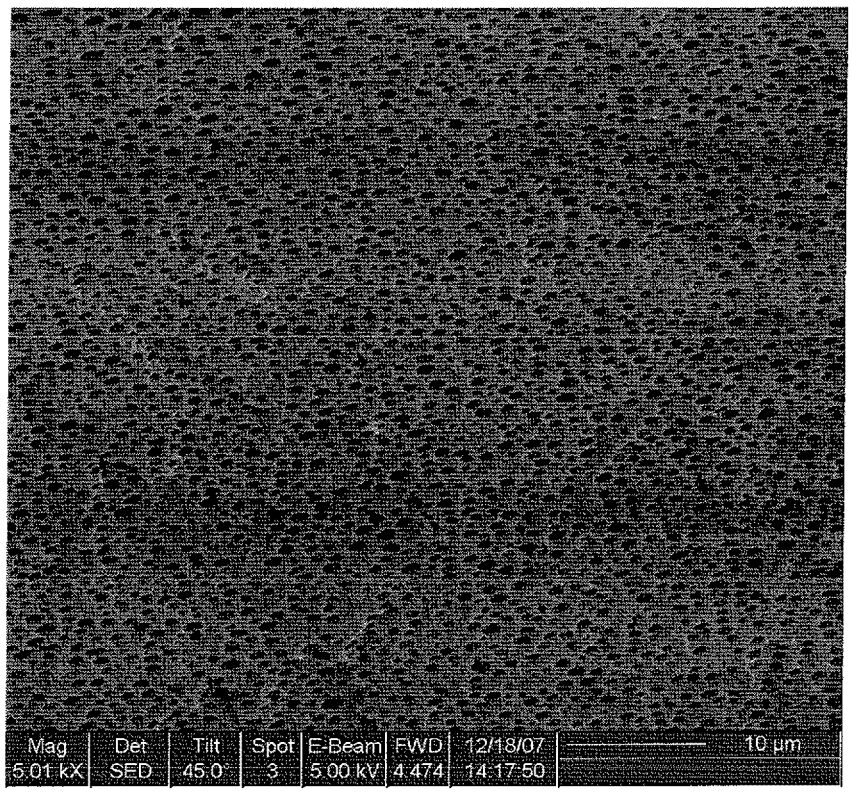
FIG. 1. Cross-sectional SEM image of a MMA:HEMA (75:25 wt/wt) porous polymer film.

In a first aspect, the invention is directed to a tooth-whitening composition. The tooth-whitening composition contains at least two components: i) a substantially water-insoluble and substantially non-degradable polymeric matrix, and ii) gas-filled or liquid-filled pores (bubbles) embedded with the polymeric matrix, wherein the gas- or liquid-filled bubbles have a size ranging from about 100 nm to about 5 μm.

Besides being water-insoluble and substantially non-degradable in an oral environment, the polymer matrix is non-toxic, resistant to microbial growth, and capable of adhering to the surface of a tooth. The polymer can be both thermoplastics and thermosets, which can be synthesized through chain polymerization and step growth polymerization.

In a particular embodiment, the polymer matrix is substantially non-degradable (i.e., durable) by maintaining its morphological integrity over an extended period of time (e.g., days, weeks, or months) with substantially imperceptible deterioration or erosion while in an oral environment. For example, in particular embodiments, the overall weight, area of coverage, or thickness of a polymer film of the composition on a tooth will be maintained within ±20%, and more preferably within ±10%, over a 30-day period. In other embodiments, the polymer film is designed to last between brushings or dental hygiene events. Preferably the polymer matrix also inhibits binding or adherence of microbes thereon (e.g., inhibition of biofilm formation).

The polymeric matrix should also be capable of adhering to the surface of a tooth. Typically, inclusion of polar groups in the polymer matrix facilitates adhesion of the polymeric matrix onto a tooth. Some types of particularly suitable polar groups for this purpose include carboxylic acid, amine, ester, amide, hydroxyl, urethane, urea, and urea groups. A substantially non-polar (e.g., hydrocarbon or fluorohydrocarbon) polymer matrix without polar groups is expected to interact poorly with the surface of a tooth, and therefore, those types of polymers are not preferred.

In one embodiment, the composition (i.e., polymer matrix) is in a solid form, typically pre-shaped as a film ready for application onto a tooth. As used herein, a "solid form" of the composition is used to mean a form of the composition that does not flow, cannot be impressed by a localized pressure, and which rigidly keeps its form under typical (standard) conditions. The composition can have the properties of a thermoplastic or a thermoset material. Preferably, the composition is not brittle, i.e., is resistant to chipping or cracking. The composition must be capable of remaining a solid during use on teeth in an oral environment.

The composition can alternatively be in a non-solid form (e.g., a liquid or paste) before or during application of the composition onto a tooth. However, the composition, when not in solid form, has the property of being solidifiable by chemical alteration. By "chemical alteration" is meant a change in the chemical bonding structure of the composition, as can be provided by such processes as radiative, thermal, or chemical curing. Accordingly, when the composition is in the non-solid state, it possesses appropriate chemical functionality to allow for solidification. The solidifying process can also include simply drying the composition (or a solution thereof) onto a tooth.

In a preferred embodiment, the polymer matrix is (or includes) a vinyl polymer. Some types of vinyl monomer units from which the vinyl polymer can be synthesized include styrene (e.g., polystyrene or a copolymer of styrene), vinylacetate (e.g., poly(vinylacetate) or a copolymer of vinylacetate), ethylene (e.g., polyethylene or a copolymer of ethylene), propylene (e.g., polypropylene or a copolymer of propylene), vinyl toluene (e.g., polyvinyl toluene or a copolymer of vinyltoluene), chloro-containing vinyl monomers, such as vinylchloride (e.g., poly(vinyl chloride) or a copolymer of vinyl chloride), and fluoro-containing vinyl monomers, such as vinyl fluoride, tetrafluoroethylene, perfluoroalkoxyvinyl monomers, and vinylidene fluoride (e.g., poly (vinylidenefluoride)), and polymers or copolymers of any of these monomers.

The vinyl polymer can be a homopolymer, or alternatively, a copolymer derived from two or more different types of vinyl monomers (units). Some examples of different kinds of copolymers considered herein include alternating copolymers, block copolymers, graft copolymers, random copolymers, and combinations thereof.

More preferably, at least a portion of the vinyl polymer is derived from one or more monomers containing an acrylate group. In one embodiment, the vinyl polymer is composed of both non-acrylate and acrylate units. In another embodiment, the vinyl polymer is composed completely of acrylate units, wherein the acrylate units may all be chemically the same (i.e., a homopolymer) or may be chemically different (i.e., a copolymer, terpolymer or higher polymer system).

In one embodiment, at least a portion of one or more acrylate monomers are according to the formula:

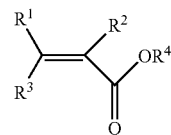

(1)

In formula (1), $R^1$, $R^2$, and $R^3$ independently represent a hydrogen atom, nitrile group, fluorine atom, chlorine atom, or a saturated or unsaturated hydrocarbon group (preferably containing 1-6 carbon atoms), and $R^4$ represents a hydrogen atom or a saturated or unsaturated hydrocarbon group (preferably containing 1-6 carbon atoms), nitrile groups, fluorine atoms, or chlorine atoms.

In a more specific embodiment to formula (1), at least a portion of one or more acrylate monomers are according to the formula:

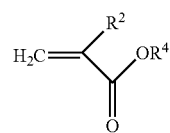

(2)

In formula (2), $R^2$ represents a hydrogen atom, nitrile group, fluorine atom, chlorine atom, or a saturated or unsaturated hydrocarbon group (preferably containing 1-3 carbon atoms), and $R^4$ represents a saturated or unsaturated hydrocarbon group (preferably containing 1-6 carbon atoms), wherein the hydrocarbon group can (i.e., optionally) be substituted by one or more nitrile groups, fluorine atoms, or chlorine atoms.

Some examples of monomers governed by formula (1) or (2) include acrylic acid, methyl acrylate, ethyl acrylate, n-propyl acrylate, isopropyl acrylate, n-butyl acrylate, isobutyl acrylate, sec-butyl acrylate, t-butyl acrylate, methyl methacrylate, ethyl methacrylate, n-propyl methacrylate, isopropyl methacrylate, n-butyl methacrylate, isobutyl methacrylate, sec-butyl methacrylate, t-butyl methacrylate, 3-methylacrylic acid, 3,3-dimethylacrylic acid, 2,3-dimethylacrylic acid, 2-fluoroacrylic acid, 2-chloroacrylic acid, methyl 2-fluoroacrylate, 2-cyanoacrylic acid, methyl 2-cyanoacrylate, ethyl 2-cyanoacrylate, n-propyl 2-cyanoacrylate, isopropyl 2-cyanoacrylate, n-butyl 2-cyanoacrylate, and isobutyl 2-cyanoacrylate.

In another embodiment, at least a portion of one or more acrylate monomers are according to the formula:

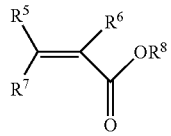

(3)

In formula (3), $R^5$, $R^6$ and $R^7$ independently represent a hydrogen atom, nitrile group, fluorine atom, chlorine atom, or a saturated or unsaturated hydrocarbon group (preferably containing 1-6 carbon atoms), and $R^9$ represents a hydrogen atom or a saturated or unsaturated hydrocarbon group (preferably containing 1-6 carbon atoms), wherein the hydrocarbon group can (i.e., optionally) be substituted by one or more nitrile groups, fluorine atoms, or chlorine atoms, and wherein at least one of $R^5$, $R^6$, $R^7$, and $R^8$ is a saturated or unsaturated hydrocarbon group substituted by at least one hydroxyl (OH) group. The number of hydroxyl groups can be, for example, 1, 2, 3, or more.

In a more specific embodiment to formula (3), $R^5$, $R^6$, and $R^7$ independently represent a hydrogen atom, nitrile group, fluorine atom, chlorine atom, or a saturated or unsaturated hydrocarbon group (preferably containing 1-6 carbon atoms), wherein the hydrocarbon group can (i.e., optionally) be substituted by one or more nitrile groups, fluorine atoms, chlorine atoms, or hydroxyl groups, and $R^8$ represents a saturated or unsaturated hydrocarbon group (preferably containing 1-6 carbon atoms) substituted by (i.e., containing) at least one —OH group.

In a further specific embodiment to formula (3), at least a portion of one or more acrylate monomers are according to the formula:

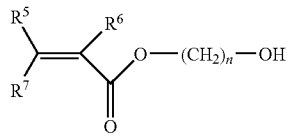

(4)

In formula (4), $R^5$, $R^6$, and $R^7$ independently represent a hydrogen atom, nitrile group, fluorine atom, chlorine atom, or a saturated or unsaturated hydrocarbon group (preferably containing 1-6 carbon atoms), wherein the hydrocarbon group can be substituted by one or more nitrile groups, fluorine atoms, chlorine atoms, or —OH groups. The subscript n can be any suitable integer (preferably at least 1 and up to 20), but more preferably represents an integer of 1 to 12, more preferably 1 to 8, and more preferably 1 to 6. In different embodiments, the subscript n may also preferably be a value of (or a maximum of value of) 5, 4, 3, 2, or 1.

In a more specific embodiment to formula (4), at least a portion of one or more acrylate monomers are according to the formula:

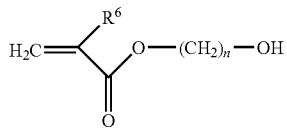

(5)

In formula (5), $R^6$ represents a hydrogen atom, nitrile group, fluorine atom, chlorine atom, or a saturated or unsaturated hydrocarbon group (preferably containing 1-6, 1-5, 1-4, or 1-3 carbon atoms), and n represents any value described above (and preferably an integer of 1 to 4), wherein the hydrocarbon group can (i.e., optionally) be substituted by one or more nitrile groups, fluorine atoms, chlorine atoms, or hydroxyl groups.

Some examples of monomers governed by formula (3), (4), or (5) include hydroxymethylacrylate, (2-hydroxyethyl)acrylate, (1-hydroxyethyl)acrylate, (3-hydroxypropyl)acrylate, (2-hydroxypropyl)acrylate, (4-hydroxybutyl)acrylate, (3-hydroxylbutyl)acrylate, (2-hydroxylbutyl)acrylate, (5-hydroxypentyl)acrylate, (4-hydroxypentyl)acrylate, (3-hydroxypentyl)acrylate, (6-hydroxyhexyl)acrylate, (5-hydroxyhexyl)acrylate, (7-hydroxyheptyl)acrylate, and (8-hydroxyoctyl)acrylate. Additional examples are provided by replacing "acrylate" in any of the preceding examples with, for example, "methacrylate" or "ethacrylate". Other examples of monomers according to formulas (3)-(5) include ethyl-2-(hydroxymethyl)acrylate, methyl-2-(hydroxymethyl)acrylate, ethyl-2-(hydroxyethyl)acrylate, 3-(hydroxymethyl)methacrylate, and 3-(hydroxymethyl)ethacrylate.

In one set of embodiments, the polymer matrix is derived from at least two acrylate monomer types (i.e., is at least a copolymer), the first monomer type according to formula (1) given above and the second monomer type according to formula (3), (4) or (5) given above. In another set of embodiments, the polymer matrix is derived from at least two acrylate monomer types (i.e., is at least a copolymer), the first monomer type according to formula (2) given above and the second monomer type according to formula (3), (4) or (5) given above. The polymer matrix can have any suitable weight ratio of monomer types according to formula (1) or (2) and monomer types according to formula (3), (4), or (5). In different embodiments, the ratio between non-hydroxylated monomers (i.e., formula (1) or (2)) to hydroxylated monomers (i.e., formula (3), (4), or (5)) is, for example, 95:5, 90:10, 85:15, 80:20, 75:25, 70:30, 65:35, 60:40, 55:45, 50:50, 45:55, 40:60, 35:65, 30:70, 25:75, 20:80, 15:85, 10:90, or 5:95.

The acrylate monomer can also be an ethylenically unsaturated dicarboxylic acid. Some examples of such monomers include fumaric acid, maleic acid, and 3-butenoic acid.

The acrylate unit can also contain more than one acrylate group, e.g., a diacrylate, triacrylate, or higher acrylate-containing molecule. Such polyacrylate molecules are typically used as crosslinkers. As used herein, the term "acrylate" is meant to include "methacrylate," "cyanoacrylate," and other derivatized acrylates, and thus, "diacrylate," "triacrylate," and "polyacrylate," is meant to include all such derivatized acrylates. One class of polyacrylate molecules are those based on diols, such as ethylene glycol dimethacrylate (CAS No. 97-90-5, EGDMA), and dimethacrylates based on higher chain diols, such as, for example, propanediol, butanediol (e.g., 1,3-butanediol and 1,4-butanediol), pentanediol, neopentyl glycol, hexanediol (e.g., 1,6-hexanedioldimethaerylate, HDDMA, CAS No. 6606-59-3), heptanediol, octanediol, and their ethoxylated and propoxylated derivatives, and the like. Another class of polyacrylate molecules are those based on repeating units of diols, such as diethyleneglycol dimethacrylate (CAS No. 2358-84-1), triethyleneglycol dimethacrylate, propylene glycol (e.g., 2,3-dihydroxypropyl) dimethacrylate, and tetraethyleneglycol dimethacrylate (TEDMA). Another class of polyacrylate molecules are those based on bis-phenol A, e.g., 2,2'-bis[4-(3-methacryloxy-2-hydroxypropoxy)phenyl]propane (i.e., "bis-GMA"), which is the addition product of bis-phenol A and glycidyl methacrylate. Other diacrylates based on bis-phenol A include ethoxylated and propoxylated bis-phenol A dimethacrylates (e.g., ethoxylated bis-phenol A dimethacrylate, i.e., EBPDMA or EBPADMA). Another class of polyacrylate molecules are the diacrylates, triacrylates, and higher functionalized acrylates based on polyols, such as those based on trimethylolpropane, glycerol, citric acid, or pentaerythritol (e.g., 3-(acryloyloxy)-2-hydroxypropyl methacrylate; or 2-ethyl-2-(hydroxymethyl)-1,3-propanediol triacrylate (TMPTA); or di(trimethylolpropane)tetraacrylate; or pentaerythritol tetraacrylate, triacrylate, or diacrylate; or glycerol dimethacrylate or trimethacrylate; and their ethoxylated and propoxylated derivatives). Yet another class of polyacrylate molecules are the urethane polyacrylates, such as 7,7,9 (or 7,9,9)-trimethyl-4,13-dioxo-3,14-dioxa-5,12-diazahexadecane-1,16-dioxymethacrylate and isomers, i.e., "urethane dimethacrylate" (UDMA) or "diurethane dimethacrylate" or (DUDMA), e.g., CAS No. 74389-53-0 or 72869-86-4), and polyurethane dimethacrylate (PUDMA). Yet another class of polyacrylate molecules are polycarbonate-based polyacrylates (e.g., polycarbonate dimethacrylate, PCDMA), which is typically the condensation product of two parts of a hydroxyalkylmethacrylate and one part of a bis(chloroformate). Yet another class of polyacrylate molecules are those based on phosphate or phosphoric acid, e.g., bis-[(2-(methacryloyloxy)ethyl]phosphate. Still another class of polyacrylate molecules are the bis-acrylamides (e.g., N,N'-ethylenebis(acrylamide) or N,N'-(1,2-dihydroxyethylene)bisacrylamide). Still yet, another class of polyacrylate molecules are the triazine or isocyanurate di- and tri-methacrylates, e.g., 1,3,5-triacryloylhexahydro-1,3,5-triazine or tris[2-(acryloyloxy) ethyl]isocyanurate.

The polymer matrix can also include any of the ionomer polymer compositions known in the art, as long as the properties of the polymer matrix, as described above, are retained. The ionomer compositions typically include a percentage by weight of an acid functionality of or less than 50%. In different embodiments, the acid functionality can be, for example, at or less than 40%, 30%, 20%, 10%, 5%, or 1%.

The polymer matrix can also include (or be composed of) a copolymer containing polymer components or units of different polymer classes. Some examples of such copolymers include polyvinyl-polyurethane, polyvinyl-polyurea, polyvinyl-polyamide, polyvinyl-polycarbonate, polycarbonate-polyurethane, and polycarbonate-(phenol-formaldehyde) types of copolymers.

As used herein, the term "hydrocarbon group" refers to a chemical group containing only carbon and hydrogen, unless the presence of one or more heteroatoms is indicated. The hydrocarbon group can be any hydrocarbon group, i.e., straight-chained or branched, saturated or unsaturated, aliphatic or aromatic, and cyclic or polycyclic. In different embodiments, the hydrocarbon group may preferably contain no more than about 20 carbon atoms, or no more than 18 carbon atoms, or no more than 12 carbon atoms, or no more than 6 carbon atoms. In particular embodiments, the hydrocarbon group may contain no more than 5, 4, or 3 carbon atoms. In several embodiments, the hydrocarbon group contains at least 1, 2, or 3 carbon atoms. Any range of carbon atoms between the minima and maxima set forth above are suitable herein. For example, in different embodiments, the hydrocarbon group can preferably have 1-20, 1-18, 1-12, 1-8, 1-6, 1-5, 1-4, 1-3, 2-20, 2-18, 2-12, 2-8, 2-6, 2-5, 4-4, 2-3, 3-20, 3-18, 3-12, 3-8, 3-6, 3-5, 3-4, 4-20, 4-18, 4-12, 4-8, 4-6, or 4-5 carbon atoms.

Some examples of saturated straight-chained hydrocarbon groups include methyl, ethyl, n-propyl, n-butyl, n-pentyl, n-hexyl, n-heptyl, n-octyl, n-nonyl, n-decyl, and the like.

Some examples of saturated branched hydrocarbon groups include isopropyl, isobutyl, sec-butyl, t-butyl, isopentyl, neopentyl, 1,2-dimethylprop-1-yl, 1-methylpent-1-yl, 2-methylpent-1-yl, 3-methylpent-1-yl, 1,2-dimethylbut-1-yl, 2,2-dimethylbut-1-yl, and 3,3-dimethylbut-1-yl.

Some examples of saturated cyclic hydrocarbon groups include cyclopropyl, cyclobutyl, cyclopentyl, cyclohexyl, cycloheptyl, cyclooctyl, 3-methylcycloprop-1-yl, 3,4-dimethylcycloprop-1-yl, 4-methylcyclohex-1-yl, and 3,5-dimethylcyclohex-1-yl.

Some examples of saturated polycyclic hydrocarbon groups include decalin, bicyclohexyl, norbornyl, and bicyclo [4.3.0]nonane.

Some examples of unsaturated straight-chained hydrocarbon groups include vinyl, 2-propen-1-yl, 3-buten-1-yl, 2-buten-1-yl, 4-penten-1-yl, 3-penten-1-yl, 2,4-pentadien-1-yl, 5-hexen-1-yl, 3,5-hexadien-1-yl, and 1,3,5-hexatrien-1-yl.

Some examples of unsaturated branched hydrocarbon groups include 2-methyl-2-propen-1-yl, 2-methyl-2-buten-1-yl, 2-methyl-3-buten-1-yl, 2-methyl-3-penten-1-yl, 4-methyl-3-penten-1-yl, and 3-methyl-3-penten-1-yl.

Some examples of unsaturated cyclic hydrocarbon groups include cyclopentenyl, cyclohexenyl, cyclohexadienyl, and the aromatic monocyclic hydrocarbon groups (e.g., phenyl, tolyl, xylyl, and benzyl).

Some examples of unsaturated polycyclic hydrocarbon groups include naphthyl, indanyl, indenyl, anthracenyl, phenanetryl, and biphenyl.

A hydrocarbon group may include one or more oxygen atom (—O—), amino (e.g., —NH— or tert-amino), amido, ester (—C(O)O), carbonate, urea or carbamate group carbon-carbon bond interruptions, unless otherwise specified. A hydrocarbon group can also include one or more silicon-containing groups (e.g., silicon-oxide or siloxane groups).

The tooth-whitening composition of the invention includes gas- or liquid-filled compartments (i.e., pores or bubbles) embedded in the polymer matrix described above. The liquid or gas in the pores preferably possess a refractive index different from (typically lower than) the polymer matrix, and more preferably, a refractive index at least 0.1 units, and more preferably at least 0.2 units, and more preferably at least 0.3 units, and more preferably at least 0.4 units, and more preferably at least 0.5 units different than the refractive index of the polymer matrix. For example, if the polymer matrix possesses a refractive index of about 1.5, preferably the refractive index of the gas or liquid in the pores possess a refractive index of about 1.4 or less, and more preferably about 1.3 or less, and more preferably about 1.2 or less, and more preferably about 1.1 or less, and even more preferably about 1.0.

In one embodiment, the bubbles are filled with a gas. Some examples of suitable gases include air, carbon dioxide, nitrogen, argon, or a mixture thereof.

In another embodiment, the bubbles are filled with a liquid. Some examples of suitable liquids include water, an alcohol (e.g., ethanol), or a mixture thereof.

At least a portion of the bubbles have at least one size dimension (i.e., a "size" or "diameter") of at least 100 mm and up to 5 microns (hereinafter referred to as the "main range" for this parameter). In particular embodiments within this range, at least a portion of the bubbles can have a minimum size of at least 100 nm, 150 nm, 200 nm, 250 nm, 300 nm, 350 nm, 400 nm, 450 nm, 500 nm, 550 nm, 600 nm, 650 nm, 700 nm, 750 nm, 800 nm, 850 nm, 900 nm, 950 nm, 1 μm, 1.2 μm, 1.4 μm, 1.6 μm, 1.8 μm, 2 μm, 2.2 μm, 2.4 μm, 2.6 μm, 2.8 μm, or 3 μm. In other particular embodiments within the main range, at least a portion of the bubbles can have a maximum size of 4.8 μm, 4.6 μm, 4.4 μm, 4.2 μm, 4 mm, 3.8 μm, 3.6 μm, 3.4 μm, 3.2 μm, 3 μm, 2.8 μm, 2.6 μm, 2.4 μm, 2.2 μm, 2 μm, 1.8 μm, 1.6 μm, 1.4 μm, 1.2 μm, 1 μm, 950 nm, 900 nm, 850 nm, 800 nm, 750 nm, 700 nm, 650 nm, 600 nm, 550 nm, 500 nm, 450 nm, 400 nm, 350 nm, 300 nm, 250 nm, or 200 nm. Any range derived from the foregoing minima and maxima are contemplated herein. For example, in particular embodiments, the bubbles are preferably within a range of 100-5000 nm, or 100-4000 nm, or 100-3000 nm, or 100-2000 nm, or 100-1000 nm, or 200-5000 nm, or 200-4000 nm, or 200-3000 nm, or 200-2000 nm, or 200-1000 nm, or 300-5000 nm, or 300-4000 nm, or 300-3000 nm, or 300-2000 mm, or 300-1000 nm. The bubbles can have any suitable distribution of sizes, including substantially monodisperse, polydisperse, or multimodal.

The portion of bubbles within the indicated size range can be, for example, 100% of the total number of bubbles, or, for example, about 90%, 80%, 70%, 60%, 50%, 40%, 30%, 20%, 10%, or 5% of the total number of bubbles. For example, there may be provided a bubble distribution in which about 60% of the bubbles possess a size within the range of 100 nm to 5 μm, while 40% of the bubbles possess a size outside of the foregoing range (e.g., less than 100 nm or greater than 5 μm). Without being bound by any theory, it is believed that having at least a portion of the bubbles within the size range of 100 nm to 5 μm permits the bubbles to properly interact with incoming light (by having a size comparable to the wavelength of incident light) such that the optical properties of the composition on a tooth are appropriately modified to produce a whiter reflection.

Preferably, the bubbles are not substantially closed (i.e., substantially flattened) to a degree that results in a significantly reduced whitening effect. In one embodiment, the shape of the bubbles preferably approach a spherical shape (e.g., an eccentricity approaching zero). In the foregoing embodiment, the bubbles can preferably have, on average, an eccentricity of or less than 0.9, 0.8, 0.7, 0.6, 0.5, 0.4, 0.3, 0.2, or 0.1, or any range resulting from any two of the foregoing values. In another embodiment, the shape of the bubbles are preferably flattened (e.g., rod- or needle-shaped) by having, on average, an eccentricity of or greater than 0.1, 0.2, 0.3, 0.4, 0.5, 0.6, 0.7, 0.8, or 0.9, or any range resulting from any two of the foregoing values.

Preferably, the bubbles account for at least 0.1% by volume and up to about 60% by volume of the composition. In particular embodiments within this range, the bubbles may account for at least 0.2%, 0.5%, 1%, 2%, 5%, 10%, 15%, 20%, 25%, 30%, 35%, 40%, or 45% by volume of the composition. In other particular embodiments within the main range, the bubbles may account for no more than 55%, 50%, 45%, 40%, 35%, 30%, 25%, 20%, 15%, 10%, 5%, 2%, or 11% by volume of the composition. Any range derived from the foregoing minima and maxima are contemplated herein. For example, in particular embodiments, the bubbles can account for 0.5-60%, or 1-60%, or 2-60%, or 5-60%, or 10-60%, or 0.5-50%, or 1-50%, or 2-50%, or 5-50%, or 10-50%, or 0.5-40%, or 1-40%, or 2-40%, or 5-40%, or 10-40%, or 0.5-30%, or 1-30%, or 2-30%, or 5-30%, or 10-30%, or 0, 5-20%, or 1-20%, or 2-20%, or 5-20%, or 10-20% by volume of the composition.

The bubbles can be formed by any suitable process. In one embodiment, the bubbles are produced by including acid- or base-etchable particles in the polymer matrix, and then treating (etching) the particles with an acid or base to dissolve the particles such that pores remain. Some examples of acid-etchable particles include those composed of a metal carbonate, bicarbonate, hydroxide, or oxide. Some examples of base-etchable particles include those composed of metal oxides or organic acids. In another embodiment, the bubbles are produced by including water-soluble or biodegradable particles in the polymer matrix, as described above in a precursor composition, and then treating the particles with water or biodegradable conditions such that the particles are removed such that pores remain. In another embodiment, the bubbles are produced by including reactive particles in the polymer matrix, and then treating the particles with a suitable reactant which causes formation of a gas or liquid. Some examples of reactive particles include the metal carbonates, which react with an acid to form carbon dioxide and water. In yet another embodiment, the bubbles are produced by subjecting the polymeric matrix (or specialized particles embedded therein) to a physical process, such as thermolysis, radiation exposure, pressurization or depressurization, laser exposure, and related processes. In such a process, either the polymeric matrix itself or a component included therein (e.g., particles) possess a property of forming a gas or liquid when subjected to the physical process.

In another aspect, the invention is directed to a precursor composition which can be converted to a tooth-whitening composition described above. The precursor composition contains the polymer matrix described above and particles of a water-soluble or biodegradable material embedded in the polymer matrix. Water-soluble particles would also preferably be insoluble in organic media to the extent that dissolution in the polymer matrix is prevented. On contact with water and/or suitable environment where biodegradation can take place (i.e., particularly in the mouth), the particles within the precursor composition will either be solubilized and/or biodegraded such that voids (i.e., bubbles of a gas or a liquid) will result. The resulting voids will have a size range and other properties as described above. Preferably, the particles in the precursor composition have sizes within the range of about 50 nm to 5 μm, and more preferably about 50 nm to 4 μm or 50 nm to 3 μm, or 50 nm to 2 μm, or 50 nm to 1 μm, or 50 to 500 nm.

The water-soluble or biodegradable particles in the precursor composition can be composed of any non-toxic material known in the art having these properties. For example, in one embodiment, the particles of the precursor composition contain a biodegradable polyester material, such as a polylactide, polyglycolide, polycaprolactone, or a polyhydroxyalkanoate (e.g., poly-4-hydroxybutyrate, polyhydroxyvalerate, polyhydroxyhexanoate, polyhydroxyoctanoate), and their copolymers. In another embodiment, the particles contain a natural polymeric or molecular material, such as a sugar or starch. In another embodiment, the particles contain a soluble salt material, such as an alkali halide (e.g., NaCl or KCl), alkali carbonate, alkali sulfate, alkali phosphate, alkaline earth halide, alkaline earth carbonate, alkaline earth sulfate, alkaline earth phosphate, or a combination thereof.

In another aspect, the invention is directed to a tooth-whitening system. The tooth whitening system includes either the whitening composition described above or the precursor composition described above along with an application device (i.e., applicator or delivery tool) capable of delivering the composition onto a tooth. The tooth-whitening system can be, for example, in the form of a kit. The delivery tool can be any delivery tool known in the art useful for applying a liquid or paste onto teeth.

In a first embodiment, the delivery tool is referred to herein as a "gel in tray delivery system". In the gel in tray delivery system, monomers are selected based on the desired physical properties of the final polymer films. By a preferred process, these monomers are pre-mixed and combined with a photoinitiator (e.g., UV-activated). The monomers are then preferably exposed to photoinitiating (e.g., UV) light to obtain a partially polymerized viscous precursor. Exposure time is dependent on the monomer selection and the photoinitiator. Pore-forming particles (e.g., water-soluble particles) can be included at this stage if a precursor composition containing erodible particles is desired. For example, the particles can be dispersed in a suitable solvent (e.g., isopropyl alcohol) and then mixed into the viscous precursor. Additional photoinitiator and crosslinker (e.g., ethylene glycol dimethacrylate (EGDMA)) can be then added to the viscous precursor. The resulting mixture is dispensed into mouth trays that are typically custom fit. The mouth trays are inserted into the mouth to contact the teeth with the viscous precursor. After deposition of the viscous precursor onto the teeth, the coated teeth are exposed to photoinitiating (e.g., UV) light to cure the polymer pre-mix solution. If a precursor composition containing erodible particles is used, the particles within the surface film will slowly erode to develop a porous coating on the tooth surface. The resulting pores will then provide the desired optical properties, as described above.

In a second embodiment, the delivery tool is referred to herein as a "reactive film delivery system". In the reactive film delivery system, monomers are selected and preferably processed as in the first embodiment to result in a viscous precursor. Films are prepared by casting (approximately 20-500 microns) the precursor mixture onto a non-reactive and adherent backing layer. Volatile solvent is then allowed to dry off without heat. The resultant films are applied to the surface of a tooth and exposed to photoinitiating (e.g., UV) light for surface curing.

In a third embodiment, the delivery tool is referred to herein as a "paint-on delivery system". In the paint-on delivery system, films can be formed on a tooth surface by painting the composition onto the tooth surface. The composition of this solution is such that when applied to the tooth surface, a solid film can be formed on the tooth surface, either during or subsequent to application on the tooth. One way this can be accomplished is by including in the composition a solvent system which maintains the film forming materials dissolved in the composition before application onto teeth, but which cannot maintain the film forming materials soluble when contacted with saliva. If the solvent has a low enough boiling point, it may alternatively be removed by evaporation, thereby leaving a solid film of the composition. Alternatively, a heating step can be employed on the coated teeth to remove the solvent in order to hasten film formation.

Preferably, the resulting film on a tooth is no more than 350 microns thick. In different embodiments, the film may preferably be no more than 300 microns thick, 250 microns thick, 200 microns thick, 150 microns thick, 100 microns thick, 80 microns thick, 50 microns thick, 25 microns thick, 10 microns thick, 5 microns thick, or 1 micron thick. Any range between any of the foregoing values (e.g., 1-300, 1-200, 1-100 or 10-300 microns) are also suitable and contemplated herein. In particular embodiments, the film may have a thickness in the range of about 20-200 microns, 20-150 microns, 20-100 microns, 20-80 microns, or 20-50 microns thick.

In another aspect, the invention is directed to methods for applying the above-described composition or precursor composition onto teeth. Any method known in the art for applying the composition onto teeth (e.g., by any of the delivery tools described above) and obtaining an adherent solid film thereon, is suitable herein. In one embodiment, the composition is applied in solid form onto the teeth. For example, a tooth may be prepared or conditioned by any suitable process known in the art (e.g., etched with phosphoric acid or coated with an adherent) and the solid film applied and bonded onto the tooth. In another embodiment, the composition can be applied in non-solid form by any of the methods described above, and the non-solid coating treated by a solidifying film-forming process. The solidifying film-forming process can be any such process known in the art. Typically, the solidifying film-forming process involves a curing process, which typically involves a thermal, radiative, or chemical curing step. For free radical initiation, photoinitiators are typically used. The photoinitiators can include, for example, the class of iodonium salts, phosphine oxides, tertiary amines, redox cure systems, peroxides, and azo compounds (e.g., AIBN). As known in the art, the photoinitiator can be combined with any of a variety of auxiliary agents, such as a photosensitizer, accelerator, reducing agent, oxidizing agent, UV absorber, or light-sensitive compound (e.g., benzil diketones, such as DL-camphorquinone).

In a particular embodiment, the method of whitening teeth is referred to herein as a "foamed film delivery method". In the foamed film delivery method, monomers are selected to have low or limited solubility in water. Typically, hydrogen peroxide is introduced (e.g., as a 35% aqueous solution or as a non-aqueous complex with polyvinylpyrrolidone), the target concentration of hydrogen peroxide in the mixture being between 0.01 and 1% w/w. Additional thickening polymer (e.g. hydroxypropylcellulose and/or ethylcellulose) can be introduced to bring the viscosity to a desired level. Organic solvent (e.g., ethanol) can be added to control viscosity and casting behavior. A small amount of a transition metal source (e.g., iron or copper salts) can be added to assist with polymerization and foaming initiation. The film is cast and cured, such as by heating (e.g., to 40-120° C.) or UV-light exposure, or a combination thereof. During the process of casting and curing, the film polymerizes, generates foam, and sets. An additional adhesive layer can be applied to the foamed layer to provide adhesion to oral surfaces. When this foamed film is applied to teeth, it provides a whitening effect.

When the resulting film containing gas- or liquid-filled bubbles is adhered onto a tooth, the tooth appears whiter as compared to the tooth without the adherent film. The whiteness of the tooth can be assessed to be whiter by any suitable whiteness scale. The preferred whiteness scale considered herein is the CIE Lightness Index (LI) scale, which rates whiteness on a scale of 0 (no whiteness, i.e., black) to 100 (complete whiteness with no dark component). All whiteness values used herein are based on the CIE Lightness Index unless otherwise specified. Preferably, the composition of the invention, once applied as a solid film with gas- or liquid-filled pores onto teeth, can increase the whiteness of teeth by at least 5 units, and more preferably at least 10, 15, or 20 units on the CIE Lightness Index scale.

Examples have been set forth below for the purpose of illustration and to describe the best mode of the invention at the present time. However, the scope of this invention is not to be in any way limited by the examples set forth herein.

Example 1

Preparation of Films of the Whitening Composition

Monomers, methyl methacrylate (MMA) (from Acros Organics) and 2-hydroxyethyl methacrylate (HEMA) (from Aldrich Chemicals) were mixed in different weight ratios (40:60, 60:40, 75:25 or 90:10), 3 wt % photoinitiator (Darocur 1173, Ciba Specialty Chemicals Inc.) was added to 2.5 ml of the monomer mixture and this exposed to UV light (UVP Blak-Ray ~8 mW/cm$^2$) to obtain the partially polymerized viscous precursor. Monomer mixtures containing MMA and HEMA in volume ratios of 40:60 and 60:40 were exposed to UV light for 3 minutes and those containing higher amounts of MMA were exposed for 10 minutes. Silica particles of diameter 70-100 nanometer (IPA-ST-ZL, Nissan Chemical Industries Ltd.) dispersed in isopropyl alcohol were mixed in the viscous precursor in different amounts (final silica content ranging from 0.75 to 7.5 wt % of the monomer mixture). Additional photoinitiator (2 wt % of the monomer mixture) and ethylene glycol dimethacrylate (EGDMA) (1 wt % of the monomer mixture) as crosslinker were added to the viscous precursor. Polymer films were made by casting a drop of precursor on silicon wafer, which was pressed by a flat piece of poly(dimethylsiloxane) (PDMS) elastomer, followed by exposure to UV light (Oriel NUV Illumination System, Newport) at a dose of 12000 mJ/cm$^2$. This resulted in polymer-silica particles composite films with a thickness of about 200 μm. The films were then treated with hydrofluoric acid for two minutes to etch away the embedded silica particles, followed by rinsing with water and drying in a stream of air. The obtained porous film was white in color.

Example 2

Analysis of Film Whiteness

The whiteness of the films was measured by an MHT instrument in L, a, b scale, where L is the whiteness of the film on a scale of 0-100. The cross-section of the porous films was imaged by SEM (FEI Strata DB235 FIB) at an acceleration voltage of 5 kV. The pore size and density were characterized using ImageJ software.

Figure 2:
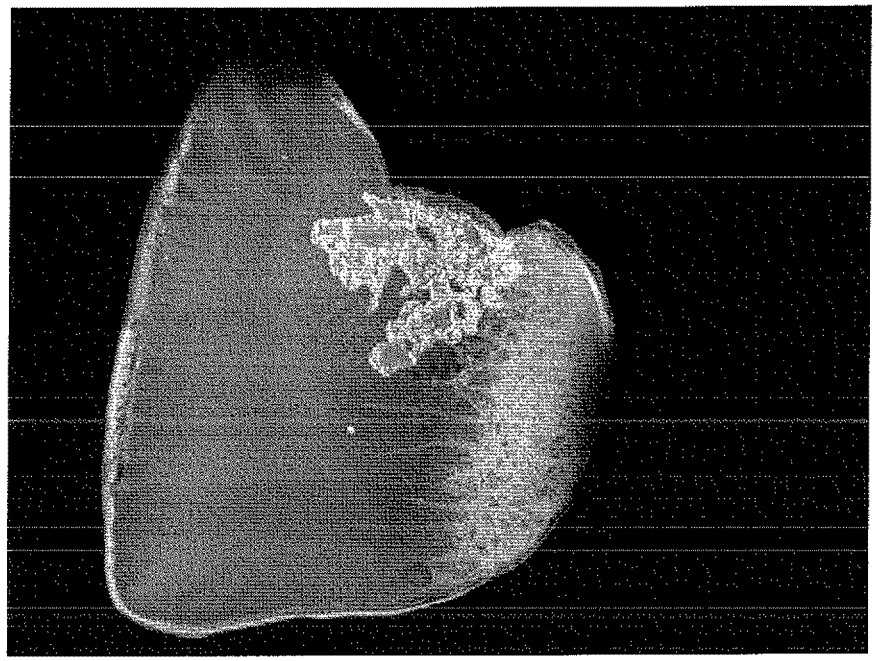
FIG. 2. Optical image of the MMA:HEMA (75:25 wt/wt) porous polymer film (of FIG. 1) showing a whiteness (L value) of 72 in air.

The porous polymer films appeared white in color. FIGS. 1 and 2 show the cross-sectional view and white appearance of one such film. With increasing silica loading in the viscous precursor, the pore volume fraction and the whiteness of the resulting porous films increases (Table 1). The pore sizes range from ~100 nanometer to 2 μm.

TABLE 1

| SiO$_2$ loading (wt % of polymer) | Polymer composition (MMA:HEMA) | Pore volume fraction (%) | Whiteness (L) |
|---|---|---|---|
| 0.75 | 40:60 | 0.16 | 1.5 |
| 1.5 | 40:60 | 4.94 | 43.7 |
| 3.75 | 40:60 | 7.67 | 65.3 |
| 3.75 | 60:40 | 9.12 | 68.4 |
| 7.5 | 40:60 | 13.56 | 76.5 |

Figure 3:
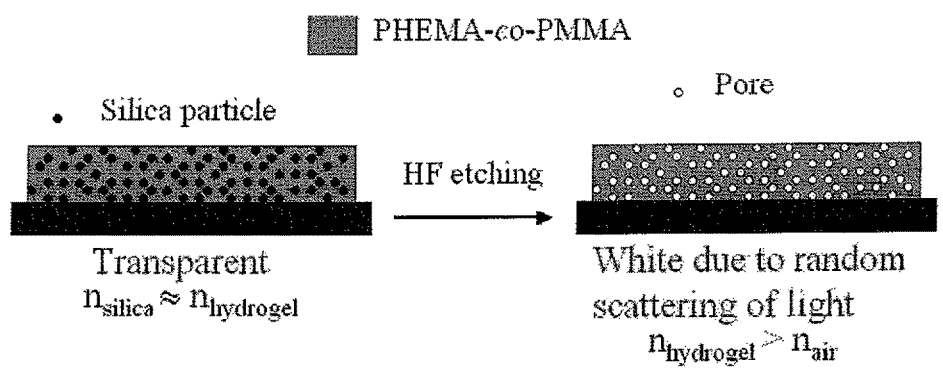
FIG. 3. Schematic showing the fabrication process of porous white films.

As shown in FIG. 3, when the polymer-silica composite film is treated with HF, the silica particles are etched away leaving a film containing a random network of pores. It is believed that the predominant etching mechanism occurring in the film is based on the following reaction:

$$SiO_2 + 4HF = 2H_2O + SiF_4(g)$$

Figure 4:
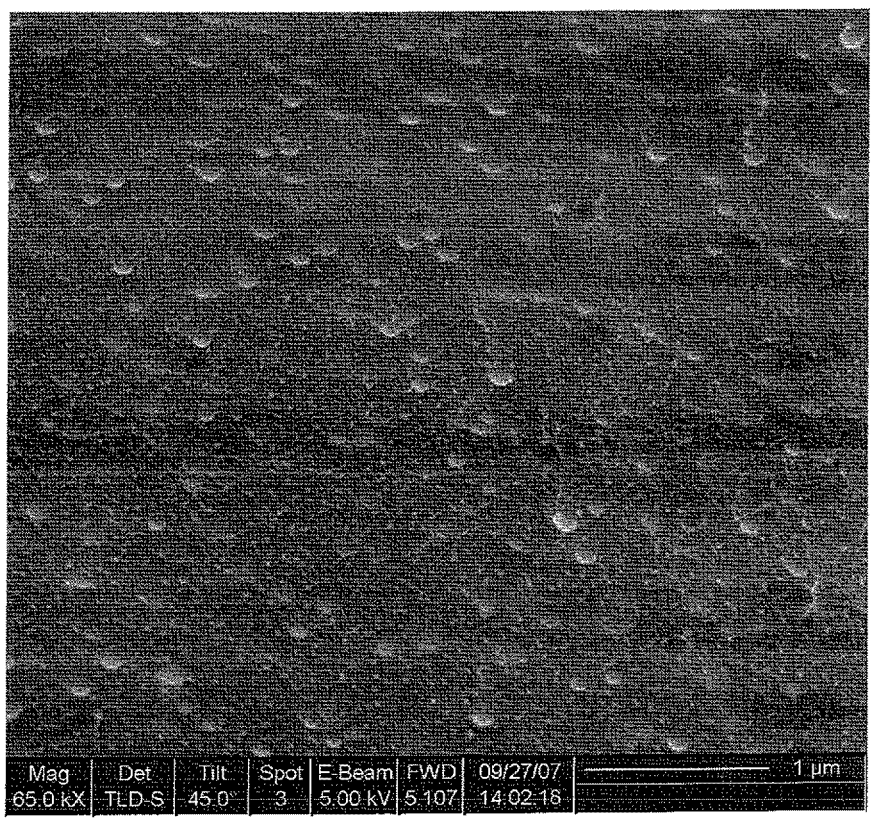
FIG. 4 SEM image of silica particles embedded in MMA-co-HEMA film.

Due to the large difference in the refractive index of air (1.0) and polymer (~0.5), the incident light is randomly scattered by the porous network, giving rise to a white appearance of the film. The pore size is in the range of >100 nanometer to ~2 km, which is comparable to the wavelength of light, resulting in effective random scattering of light. The pore size was found to be larger than that of the silica particle size (70-100 nanometer). The silica particles did not agglomerate in the polymer film and were found uniformly distributed (FIG. 4). The larger pore size may be attributed to the agglomeration of pores during the etching process while the SiF$_4$ gas is formed and diffused throughout the film.

Figure 5:
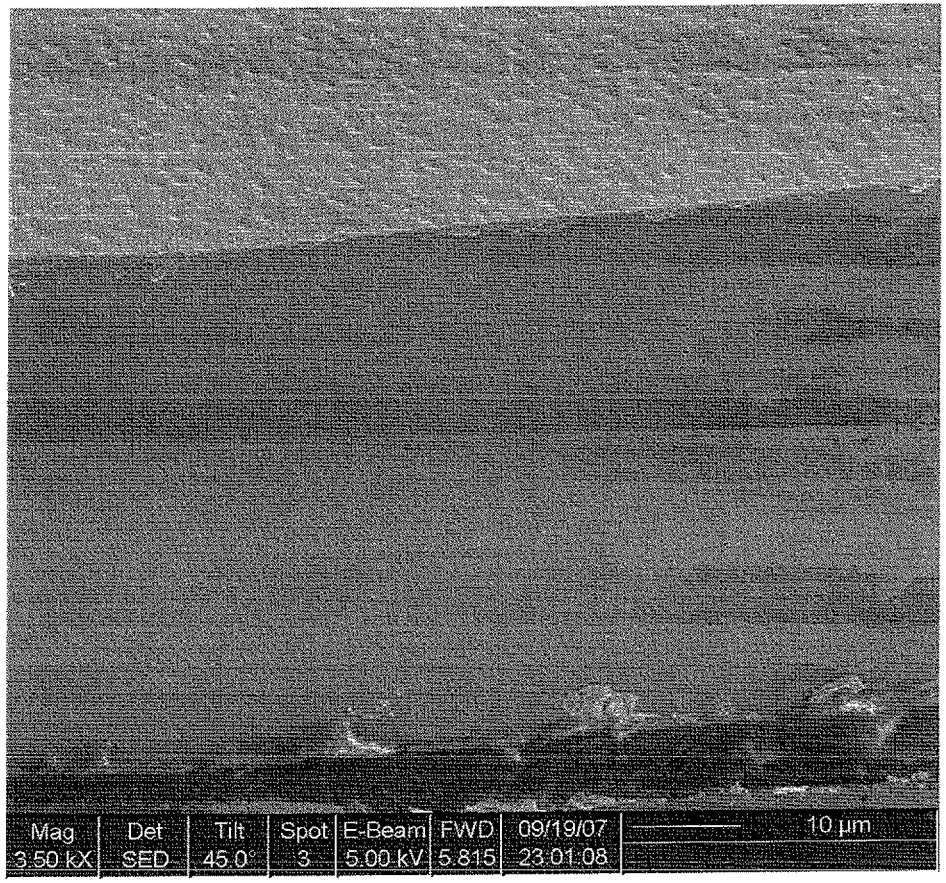
FIG. 5. Cross-sectional SEM image of neat polymer film of FIG. 4 after HF treatment.

To confirm this explanation, the cross-section of the neat polymer films that were treated with HF were examined. No pores were observed (FIG. 5) and the films remained transparent. The results validate the concept that the whiteness was caused by pore formation, and that evolution of the pore was due to gas diffusion during the etching process. Pore characteristics at various silica loadings are shown in Table 2 below.

Whiteness as a function of pore density and pore volume fraction is shown in Table 3 below. As shown by Table 3, at least for the HEMA/MMA system studied, whiteness generally increases with pore volume fraction.

Table 4 shows the effect of time elapsed after HF etching as well as MMA weight percentage on HEMA-MMA film whiteness. As shown by the table, the HEMA-MMA films show a general trend of increasing in whiteness value with increase in MMA weight percentage. HEMA-MMA films of higher MMA content also appear to follow a general trend of increasing in whiteness value with increasing time elapsed after HF etching

TABLE 2

Pore Characteristics at Various Silica Loadings
SiO$_2$ diameter ~70-100 nm

| SiO$_2$ loading (wt %) | Particle density (10$^{18}$/m$^3$) | Pore diameter (nm) | | Cross-sectional area coverage (%) | | Pore density (10$^{18}$/m$^3$) | |
|---|---|---|---|---|---|---|---|
| | | Large | Small | Large | Small | Large | Small |
| HEMA:MMA = 60:40 | | | | | | | |
| 1.5 | 16.7 | 650 | 270 | 4.5 | 4.9 | 0.05 | 0.8 |
| 3.8 | 41.6 | 784 | 162 | 5.7 | 7.7 | 0.04 | 7.2 |
| 15 | 159.8 | 1092 | | 42.97 | | 0.31 | |
| HEMA:MMA = 40:60 | | | | | | | |
| 3.8 | 41.6 | 402 | 200 | 7.2 | 9.1 | 0.4 | 4.9 |
| 7.5 | 82.0 | 396 | | 13.6 | | 1.2 | |

TABLE 3

Whiteness vs. Pore Density and Pore Volume Fraction

| Pore Volume Fraction (%) | Pore Density (10$^{18}$/m$^3$) | Whiteness |
|---|---|---|
| 0.16 | 1.2 × 10$^{-4}$ | 1.5 |
| 4.84 | 2.2 | 57.7 |
| 7.67 | 7.2 | 65.3 |
| 9.12 | 4.9 | 68.4 |
| 13.56 | 1.2 | 76.5 |

TABLE 3-continued

Whiteness vs. Pore Density and Pore Volume Fraction

| Pore Volume Fraction (%) | Pore Density ($10^{18}/m^3$) | Whiteness |
|---|---|---|
| 20.2 | 3.7 | 76.9 |
| 25.65 | 3.7 | 81.0 |

TABLE 4

Whiteness of HEMA-MMA films with 7.5 wt % 70-100 nm silica.

| | MMA wt % | | |
|---|---|---|---|
| Time (hrs) | 60 | 75 | 90 |
| 1.5 | 58, 50 | 79, 75, 67 | 78 |
| 4.5 | 45, 41 | 74, 75, 69 | 82 |
| 25 | — | 79, 79, 75 | 90 |

Figure 6:
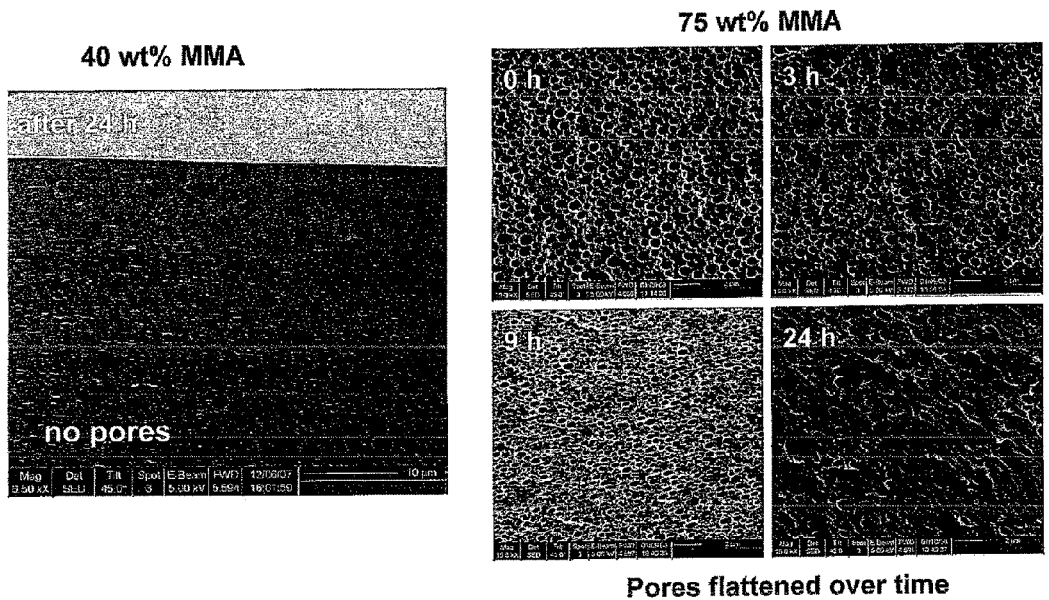
FIG. 6 Micrographs of HEMA-MMA films with 7.5 wt % 70-100 nm silica etched by HF (showing effect of time after etching and MMA wt % on pore structure).

FIG. 6 shows the effect of time elapsed after HF etching as well as MMA weight percentage on pore structure in HEMA-MMA films. As shown by the figure, the HEMA-MMA films show a general trend of flattening with increasing time elapsed after HF etching. Whiteness values increase as flattening becomes more pronounced for 75 wt % MMA samples. For 40 wt % MMA samples, whiteness decreases since the pores flatten completely.

In addition, it is shown in FIG. 6 that HEMA-MMA films containing a higher MMA weight percentage (e.g., 75 wt %) are more resistant to pore flattening than HEMA-MMA films of lower MMA weight percentage (e.g., 40 wt %). For example, 24 hours after HF etching, HEMA-MMA films of 40 wt % MMA contain nearly completely flattened pores, whereas HEMA-MMA films of 75 wt % MMA contain pores that are slightly flattened.

Table 5 shows the effect of wetness (moisture) on whiteness values in HEMA-MMA films varying in MMA weight percentage. As shown in the table, a HEMA-MMA film of 25:75 weight ratio was found to possess a whiteness value of 78.6 in the dry state, which reduced in value to 61.5 when wetted. Surprisingly, when the film was re-dried, the whiteness of the film increased again to approximately the starting value. Also shown in the table is the surprising result that a HEMA-MMA film of higher MMA weight percentage exhibits less of a reduction in whiteness value upon exposure to moisture. For example, a 10:90 HEMA:MMA film substantially maintains the starting whiteness index of the dry state even after moistening.

TABLE 5

Whiteness of HEMA-MMA films with 7.5 wt % 70-100 nm silica

| Film | Dry | Wet | Re-dry |
|---|---|---|---|
| 25:75 HEMA:MMA | 78.6 | 61.5 | 78.7 |
| 10:90 HEMA:MMA | 90.7 | 90.3 | — |

Though HEMA-MMA films of greater MMA weight percentage appear to show superior qualities in maintaining pore integrity and moisture resistance, increasing the MMA weight percentage also increases brittleness of the film. Therefore, it is important in practicing the present invention to find a composition of optimal PMMA or non-swellable polymer weight percentage that can provide the advantages described above while not rendering the film excessively brittle. In different embodiments, the appropriate MMA weight percentage can be, for example, at or greater than 10 wt %, 20 wt %, 30 wt %, 40 wt %, 50 wt %, 60 wt %, 70 wt %, 80 wt %, or 90 wt %.

While there have been shown and described what are presently believed to be the preferred embodiments of the present invention, those skilled in the art will realize that other and further embodiments can be made without departing from the spirit and scope of the invention described in this application, and this application includes all such modifications that are within the intended scope of the claims set forth herein.

What is claimed is:

1. A tooth-whitening solid film composition comprising:
(i) a water-insoluble and substantially non-degradable matrix component capable of adhering to the surface of a tooth, wherein said matrix component is a solid polymer matrix comprising a vinyl-addition polymer, wherein at least a portion of said vinyl-addition polymer is derived from at least two monomer types, each containing an acrylate group, the first monomer type according to the formula:

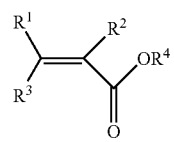

(1)

wherein $R^1$, $R^2$, and $R^3$ independently represent a hydrogen atom, nitrile group, fluorine atom, chlorine atom, or a saturated or unsaturated hydrocarbon group containing 1-6 carbon atoms, and $R^4$ represents a hydrogen atom or a saturated or unsaturated hydrocarbon group containing 1-6 carbon atoms, wherein said hydrocarbon group can be substituted by one or more nitrile groups, fluorine atoms, or chlorine atoms; and the second monomer type according to the formula:

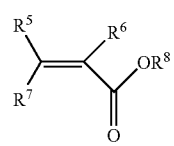

(3)

wherein $R^5$, $R^6$, and $R^7$ are independently selected from a hydrogen atom, nitrile group, fluorine atom, chlorine atom, and a saturated or unsaturated hydrocarbon group containing 1-6 carbon atoms optionally substituted by one or more groups selected from nitrile groups, fluorine atoms, chlorine atoms, and hydroxyl groups; and $R^8$ is a hydrogen atom or a saturated or unsaturated hydrocarbon group containing 1-6 carbon atoms optionally substituted by one or more groups selected from nitrile groups, fluorine atoms, chlorine atoms, and hydroxyl groups; wherein at least one of $R^5$, $R^6$, $R^7$, and $R^8$ is a saturated or unsaturated hydrocarbon group substituted by at least one hydroxyl group, provided that the composition according to Formula (1) is present in an amount from 40 wt % to 95 wt % with respect to the total weight of Formulas (1) and (3); and
(ii) air-filled pores embedded in said matrix component, wherein the pore sizes range from about 100 nm to about 2 microns, the pores account for about 5% to about 60% by volume of the solid film composition, and the film is no more than 350 microns thick and has increased whiteness.

2. The composition of claim 1, wherein the pore and polymer matrix components possess a difference in refractive index of at least 0.1.

3. The composition of claim 1, wherein the film is no more than 300 microns thick.

4. The composition of claim 1, wherein said solid film has a thickness in the range of about 20-100 microns.

5. The composition of claim 1, wherein the composition is capable of increasing the CIE lightness index of a tooth by at least 10 units.

6. The composition of claim 1, wherein the composition is capable of increasing the CIE lightness index of a tooth by at least 20 units.

7. The composition of claim 1, wherein at least 80% of the pore sizes range from about 100 nm to about 1 micron.

8. The composition of claim 1, wherein at least 80% of the pore sizes range from about 200 nm to about 1 micron.

9. A method for whitening teeth, the method comprising applying the tooth-whitening composition of claim 1.

10. The composition of claim 1, wherein the composition according to Formula (1) is present in an amount from 75 wt % to 95 wt % with respect to the total weight of Formulas (1) and (3).

* * * * *